United States Patent [19]
Fabbri, deceased et al.

[11] Patent Number: 4,809,702
[45] Date of Patent: Mar. 7, 1989

[54] METHOD FOR RECORDING FOETAL MOVEMENTS DURING PREGNANCY AND APPARATUS FOR CARRYING OUT THE SAID METHOD

[75] Inventors: Marcel Fabbri, deceased, late of Besançon; Marie O. P. Fabbri-Ollinger, legal representative, Fresnes en Woevre; Jean-François Brandon, Brunoy; Claude Colette, Besancon Cedex; Bernard Weichlein, Besancon, all of France

[73] Assignee: Universite de Franche-Comte, France

[21] Appl. No.: 119,062

[22] Filed: Nov. 10, 1987

Related U.S. Application Data
[63] Continuation-in-part of Ser. No. 441,999, Nov. 16, 1982, abandoned.

[30] Foreign Application Priority Data
Nov. 20, 1981 [FR] France .................. 8121823

[51] Int. Cl.$^4$ .............................................. A61B 10/00
[52] U.S. Cl. ............................. 128/661.07; 128/662.04
[58] Field of Search ................. 128/660, 661, 24 A

[56] References Cited
U.S. PATENT DOCUMENTS

| | | | |
|---|---|---|---|
| 3,584,618 | 6/1971 | Reinhard et al. | 128/723 |
| 3,780,725 | 12/1973 | Goldberg | 128/661 |
| 3,926,177 | 12/1975 | Hardway, Jr. et al. | 128/722 |
| 4,122,427 | 10/1978 | Korsh | 128/721 X |

FOREIGN PATENT DOCUMENTS

| | | | |
|---|---|---|---|
| 2640682 | 3/1977 | Fed. Rep. of Germany | 128/662 |
| 2045857 | 11/1971 | France | 128/663 |

OTHER PUBLICATIONS
McDicken, W. N. et al, "An Ultrasonic Real-Time Scanner/Pulsed Doppler and TM Facilities for Foetal Breathing", UTS in Med. & Biol. V4 (1979), pp. 333–339.
Wells, P. N. T., "A Range-Gated UTS Doppler System", MBE V7, pp. 641–652 (1969).
McHugh, R. et al, "An Ultrasonic Pulsed Doppler Instrument", UTS in Med. & Biol., V3, #4, pp. 381–384, Pergamon Press, 1978.

*Primary Examiner*—Francis Jaworski
*Attorney, Agent, or Firm*—Steinberg & Raskin

[57] ABSTRACT

A method and an apparatus for recording foetal movements comprising a pick-up which forms part of an ultrasonic transducer connected, on the one hand, to an electric wave emitter device and, on the other hand, to a device for receiving and analyzing the electric waves obtained from the ultrasonic waves which have been reflected by the foetus and received by the transducer.

5 Claims, 2 Drawing Sheets

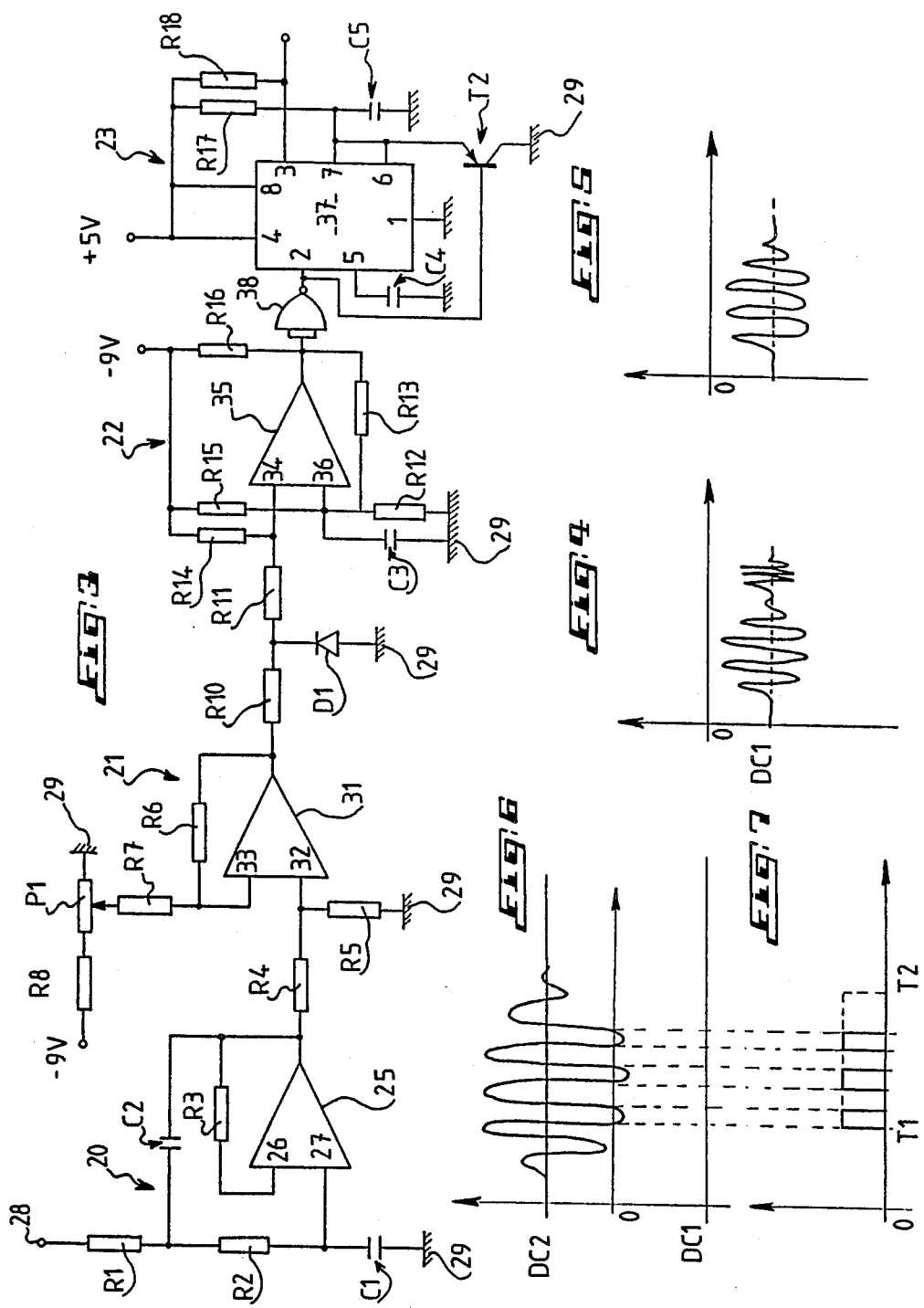

METHOD FOR RECORDING FOETAL MOVEMENTS DURING PREGNANCY AND APPARATUS FOR CARRYING OUT THE SAID METHOD

BACKGROUND OF THE INVENTION

This is a continuation-in-part application of Ser. No. 441,999 filed Nov. 16, 1982, and now abandoned.

The present invention has for a subject matter a method for counting movements, especially foetal movements during pregancy, and an apparatus for carrying out the said method.

The term "foetal movements" covers all movements of the foetus, i.e. the displacements of a foetus as a whole and of one or several parts thereof. It is known that the movements of the foetus constitute a criterion of its health. An increase or a decrease in the foetal movements compared to a normal value specific to each foetus is a sign of bad state of health.

In view of tnis fact, methods and devices have been developed for measuring the foetal activity, especially for detecting the very intense movements of the whole body of the foetus and of the sporadic kicks at the wall of the embryo sac, sufficiently strong to move the body and displace the foetus from its initial position. The known methods and devices are based on the use of a pick-up adapted to produce electric signals capable of representing a movement of the foetus and a device for analysing the electric signals proceeding from the pick-up, for detecting signals originated by the movement of the foetus, as well as a counter which is incremented every time a movement phase is detected.

Such known devices and methods suffer from considerable drawbacks due to the fact that the detection of the movements takes place at the surface of the mother's abdominal skin, by means of displacement pick-ups. It results therefrom that the known devices are insensitive to the movements of the foetus, which are not passed on to the skin. Moreover, the measurements are punctual ones, thus requiring the use of several pick-ups.

SUMMARY OF THE INVENTION

The present invention has as its purpose to provide a method and an apparatus—a counter of the foetal movements—which do not suffer from the drawbacks, just set forth, of the prior art.

In order to achieve this purpose, the method according to the invention is characterized in that the foetal movements are detected through the skin by emitting ultrasonic waves in the mother's abdominal portion and by analysing the reflected waves.

According to an advantageous characterizing feature of the method of the invention, the detection of the foetus movement is effected by analysing the frequencies of the reflected waves having undergone a change in frequency due to the DOPPLER effect produced by a movement of the foetus.

The apparatus for carrying out the method according to the invention is characterized in that the pick-up forms part of an ultrasonic transducer connected, on the one hand, to an electric wave transmitter and, on the other hand, to a device for analysing the electric waves obtained from the ultrasonic waves which have been reflected by the foetus and received by the transducer.

According to an advantageous characterizing feature of the invention, the transducer, the transmitter and the analysing devices as well as the counter are mounted in a case which is portable by being applied to the surface of the mother's abdominal skin.

BRIEF DESCRIPTION OF THE DRAWINGS

The invention will be better understood and other purposes, characterizing features, details and advantages of the latter will appear more clearly as the following explanatory description proceeds with reference to the appended diagrammatic drawings given solely by way of example illustrating one form of embodiment of the invention and wherein:

FIG. 3 shows the circuit of a receiver-analyser device according to the invention; and FIGS. 4 to 7 are graphs of signals proceeded by the circuit of FIG. 3 at different points thereof.

DESCRIPTION OF THE PREFERRED EMBODIMENTS

Figure 1:
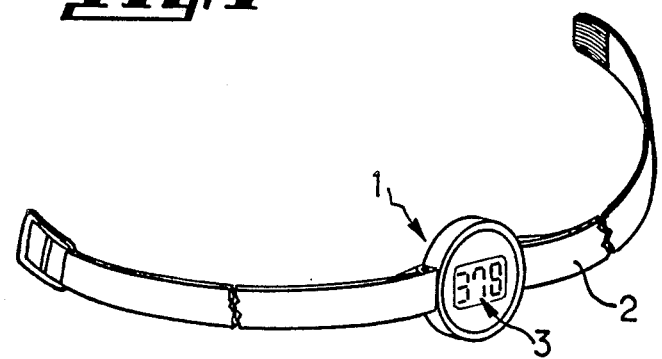
FIG. 1 is a perspective view of the apparatus for recording foetal movements, according to the present invention.

As illustrated in FIG. 1, all the devices of the electronic system of the apparatus for recording and counting foetal movements, according to the invention, are enclosed in a case 1, e.g. cylindrical in shape and of appropriate dimensions to be portable by being applied to the surface of the abdominal skin, preferably near the umbilicum. It is positioned either by being interposed between the maternity corset and the abdomen or by means of the strap 2 in case such a corset is not used. The case 1 is provided with a digital display unit 3, e.g. of the type using light-emitting diodes or liquid crystals. The function of the display unit is to display at any moment the number of foetal movements. According to FIG. 1, it is provided on the upper surface of the case, but it may, as well, be located on its edge. The display unit may also be designed in the form of a graduated dial and a pointer. The case may be about 8 cm in diameter and 2 cm in height. These values are given only by way of example and are not limitative.

Figure 2:
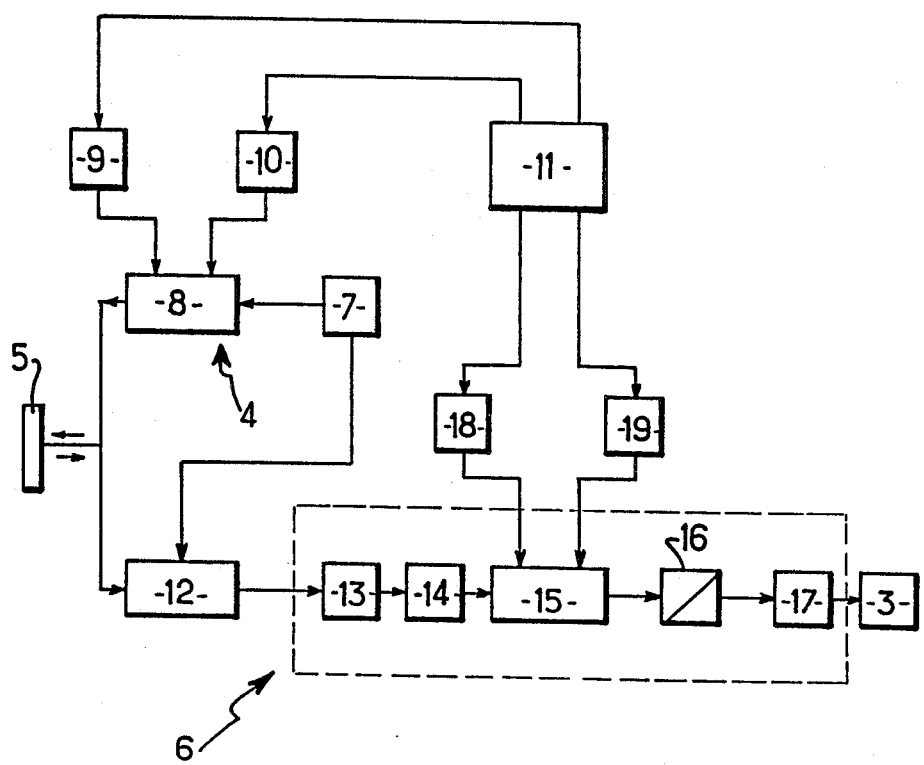
FIG. 2 is a block diagram illustrating the structure of the electric circuit of the apparatus according to FIG. 1.

According to the block diagram of FIG. 2, the electronic system enclosed in the case 1 comprises an electric wave emitter device 4, an ultrasonic transducer device 5 and a receiver and analyser device 6 for the waves resulting from the ultrasonic waves reflected by the foetus. The transducer advantageously operates in the frequency range of from 1 to 10 Mcps, which is the frequency range that is most appropriate to the human body.

The emitter device 4 includes an oscillator 7 and an emitter 8 connected to the oscillator 7 and associated with control circuits 9 and 10 for controlling the beginning of the emission and the duration of the emission, under the action of a time base 11. There can thus be obtained a pulsatory emission of ultrasonic waves.

The receiver-analyser system 6 comprises a series connection of a receiver element 12, a filter 13 tuned to a frequency band, an amplifier 14, eventually a controlled gate device 15, a foetal movement detector 16, a counter 17 and the display device 3 already mentioned in the description of FIG. 1. The counter 17 is capable of zero resetting. The gate device 15 is controlled by a circuit 18 for opening the same and thus starting the observations and by a circuit 19 for controlling the duration of gate opening or of observation, both under the action of the time base 11. The detector 10 is designed to detect the beginning and the end of a foetus movement. This double function is illustrated by the division of the block 16 into two parts. It is the detection of the end of the movement that controls the incrementing of the counter 17. This means that n the course of one movement or one phase of movements, the counter performs only one step forward. The filter 13 is designed to eliminate all the waves produced by undesired echoes.

The transducer device 5 may be constituted by two transducers, one for emission and the other for reception. However, it may be constituted by a single transducer fulfilling both functions.

The analysing system structure just described allows two modes of analysis—frequency analysis and time analysis—each of which presents certain peculiarities wnich will appear from the following description of the operation of the apparatus according to the invention.

The frequency analysis uses the Doppler effect, i.e., the change in frequency to which the reflected waves are subjected when the foetus moves, which foetus may be considered as a reflecting surface in displacement. The difference between the frequency of the waves emitted and that of the waves reflected is proportional to the speed of displacement of the surface, i.e., of the movement of the foetus.

FIG. 3 shows an embodiment of the receiver-analyser system 6 which is particularly adapted for accomplishing a frequency analysis and is based upon continued emission of ultrasonic waves. This system comprises a series connection of a low-pass filter 20, an offset circuit 21, a zero crossing detector 22 and a monostable multivibrator 23 the output signal of which increments the counter 17 shown on FIG. 2.

The low-pass filter 20 is conceived to have a cut-off frequency for instance of 250 cps corresponding to the frequency band of the transducer 5. The filter includes essentially an operational amplifier 25 having a negative input 26 and a positive input 27. Between the input 28 of the filter and the ground 29, there is provided a series connection of two resistors $R_1$, $R_2$, and a capacitor $C_1$. The input 27 of the amplifier 25 is coupled to the common terminal of resistor 2 and capacitor $C_1$. The negative input of the amplifier is coupled by a resistor $R_3$ to the amplifier output. The latter is coupled by a capacitor $C_2$ to the common terminal of resistors $R_1$ and $R_2$.

The offset circuit 21 comprises essentially an operational amplifier 31 the positive input 32 of which is coupled, on the one hand, by a resistor $R_4$ to the output of the filter amplifier 25 and, on the other hand, by a resistor $R_5$ to ground 29. The negative input 33 is coupled by a resistor $R_7$ to the sliding contact of a potentiometer $P_1$ connected between ground potential and a negative potential of for instance −9 volt, by means of a resistor $R_8$. The input 33 and tne output 31 of the amplifier are interconnected by a resistor $R_6$.

The zero crossing detector 21 comprises a series connection of two resistors $R_{10}$, and $R_{11}$ the common point of which is coupled to the anode of a diode $D_1$ connected by its cathode electrode to ground 29. The free terminal of resistor $R_{11}$ is connected to the negative input 34 of an operational amplifier 35 the positive input 36 of which is connected to ground by capacitor $C_3$ and resistor $R_{12}$ coupled in parallel relationship. The input 36 is interconnected to the amplifier output by a resistor $R_{13}$. The two inputs 34 and 36 are interconnected by resistors $R_{14}$ and $R_{15}$ the common point of which is coupled to the positive potential of 9 volt of a voltage source. A resistor $R_{16}$ is coupled between the output of amplifier 35 and positive potential of 9 volt. The amplifier of the zero crossing detector can be constituted by an integrated circuit component commercialized under the name LM393.

The monostable multivibrator 23 is esentially composed by an integrated circuit device such as the monostable multivibrator NE555. This circuit is connected in the way shown on FIG. 3, the terminals 4 and 8 being coupled to a positive potential of +5 Volts, whereas terminal 1 is directly coupled to ground and terminal 5 is coupled to ground through a capacitor $C_4$. The input terminal 2 of the multivibrator 37 is coupled by an inverter circuit 38 to the output of the zero crossing detector active component 35. A RC-circuit formed by capacitor $C_5$ and resistor $R_{17}$ is coupled to multivibrator terminal 7 interconnected with terminal 6. This latter terminal is connected to the emitter of a PNP type transistor $T_2$, the base and the collector electrodes being respectively coupled to the multivibrator terminal 2 and the ground potential 29. The output of the monostable multivibrator is formed by the terminal 3 which will be coupled to the input of counter 17 and also through a resistor $R_{18}$ to the 5 volt potential.

With reference to FIGS. 4 to 7, the working and some particularities of the system shown on FIG. 3 will be described.

FIG. 4 illustrates the wave form of the electrical signal present at the input 28 of the low-pass filter 20. This signal is a demodulated low frequency signal having a DC component $DC_1$ of for instance −3 volt. This signal is passed through the low band pass filter. The filter output signal has the shape shown on FIG. 5. In the aforesaid circuit 21, by means of the potentiometer $P_1$, the filter output signal is shifted in a positive direction so as to present the shape illustrated on FIG. 6 and to have a positive offset $DC_2$ regulated in a way that the negative peaks of the alternating signal cross the zero axis. It has been experimentally found, by means of tests, that the positive offset value $DC_2$ can be adjusted to a universally valuable value, i.e. independent from the morphological particularities of the mother and the foetus. This value is adjusted in a way allowing to obtain the signals such as shown on FIG. 6.

As results from FIG. 6, during one and the same period of foetal movements, a certain number of negative going peaks can be detected. In order to ensure that the following monostable multivibrator 23 only produce one output signal for one and the same period of movements, the RC circuit formed by capacitor $C_5$ and resistor $R_{17}$ is coupled to the integrated circuit 37 in order to avoid the working shown by the uninterrupted lines on FIG. 7 by providing a time delay between adjacent multivibrator working cycles in function of the time constant of the RC circuit. It has been found that a time constant interval of for instance 0.7 seconds will be appropriate. In the case of a foetus movement period according to the signal shown on FIG. 6, the monostable vibrator 23 will detect beginning of this movement at the time $T_1$ by producing the positively going signal shown on FIG. 7 in interrupted line which will end at the time interval, $T_1$-$T_2$ being equal to the time constant interval which will be advantageously in the order of 0.7 sec. This time constant has also been found after careful experimental works. It is the detection of the end of the movement at a time $T_2$ which will result in incrementing the counter 17.

When a pulsatory emission of ultrasonic waves is desired or when the emission of ultrasonic waves and the receiving of the reflected waves shall be accomplished at specific time periods, the system such as shown on the FIG. 2 can be used wherein the different periods of time are determined by the time base 11. For controlled observation of the reflected signals, it would be possible to provide on FIG. 3, for instance between the low-pass filter 20 and the offset circuit 21, switch means controlled by the circuits 18 and 19 shown on FIG. 2.

According to the invention, it is possible to replace the analyser system just described, i.e. the portion that is located within the dashed line on FIG. 2, with the exception, for example, of the amplifier, but including the circuits 9, 10, 18 and 19, by a microprocessor. The latter may be programmed for each case of application. Thus, the limit frequencies of the filter, the analysis frequencies and the time intervals such as the durations of emission and of observation may be programmed. The apparatus of the invention equipped with a microprocessor can provide more complex information and, for example, allow the control of the display unit 3 and the storing and control of the histogram of events. It would thus be possible to know the time elapsed between two movements of the foetus and possibly the speed of the movements. The programming can be performed for example by a programmer by means of an alphanumeric keyboard. The displacements considered as interfering displacements, such as the mother's respiration and the heartbeat of the foetus, may be entered in a storage device and constitute reference values. By comparing successively the signals received with the stored reference signals, the microprocessor can identify the signals produced by a foetal movement.

Of course, many modifications can be made to the invention without departing from its scope. For example, use can be made, instead of an analyser, of an acoustical indicator, such as a microphone, mounted downstream of the filter. It should also be noted that the invention can be used for detecting the movement of volumes other than foetuses. It can be used for the detection of heartbeat.

What is claimed is:

1. Apparatus for recording foetal movements during pregnancy, comprising ultrasonic transducer means connected, on the one hand, to an electric wave emitter device for emitting ultrasonic waves at an emission frequency and, on the other hand, to a device for reception and analysis of the electric waves obtained from said ultrasonic waves which have been reflected by a foetus and received by the transducer means connected to said reception and analysis device and which have a frequency different from the frequency of the emitted ultrasonic waves due to the Doppler frequency shift produced by a movement of the foetus, wherein said reception/analysis device comprises amplitude detector means for determining Doppler frequency shift signals having an amplitude value higher than a predetermined threshold level as significant foetal movement signals, signal selector means responsive to any significant foetal movement signals spaced from a preceding received significant signal by a time interval greater than a predetermined value and providing an output thereof, and a counter adapted to be incremented by the output of said signal selector means to thereby record movement of said foetus.

2. Apparatus according to claim 1, wherein said amplitude detector means comprises a DC offset circuit adapted to DC shift the received foetal movement signals by a DC value corresponding to said threshold level, and zero crossing detector means coupled to the output of said offset circuit for ensuring zero crossing only of signals having an amplitude greater than said threshold level.

3. Apparatus according to claim 1, wherein said signal selector means responsive to said time interval spaced signals comprises a monostable multivibrator device adapted to be set by the beginning of a time interval spaced signal and provided with means for establishing a predetermined time constant preventing resetting of said multivibrator during said time interval after the end of said signal by which said multivibrator has been set.

4. Apparatus according to claim 3, wherein the transducer means, the reception/analysis device, and the counter are mounted in a casing which is adapted to be secured to the surface of the mother's abdominal skin.

5. Apparatus according to claim 3, wherein the transducer means, the reception and analysis device, and the counter are mounted in a casing which is provided with a strap for securing and retaining said casing on the mother's abdominal skin.

* * * * *